United States Patent
Li et al.

(10) Patent No.: US 10,930,980 B2
(45) Date of Patent: Feb. 23, 2021

(54) ADDITIVE FORMULATION AND COMPOSITION FOR LITHIUM ION BATTERY AND LITHIUM ION BATTERY COMPRISING THE SAME

(71) Applicant: Industrial Technology Research Institute, Hsinchu (TW)

(72) Inventors: Yu-Han Li, Hsinchu (TW); Li-Chun Chen, Hsinchu (TW); Ming-Yi Lu, Hsinchu (TW); Jen-Chih Lo, Hsinchu (TW); Guan-Lin Lai, Hsinchu (TW); Chang-Rung Yang, Hsinchu (TW); Jung-Mu Hsu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 348 days.

(21) Appl. No.: 15/390,182

(22) Filed: Dec. 23, 2016

(65) Prior Publication Data
US 2017/0187076 A1    Jun. 29, 2017

(30) Foreign Application Priority Data
Dec. 23, 2015    (TW) .................. 104143336

(51) Int. Cl.
*H01M 10/42* (2006.01)
*H01M 4/52* (2010.01)
(Continued)

(52) U.S. Cl.
CPC ......... *H01M 10/4235* (2013.01); *H01M 4/13* (2013.01); *H01M 4/62* (2013.01);
(Continued)

(58) Field of Classification Search
None
See application file for complete search history.

(56) References Cited

U.S. PATENT DOCUMENTS

| | | | |
|---|---|---|---|
| 2007/0003832 A1 | 1/2007 | Satou et al. | |
| 2008/0131781 A1* | 6/2008 | Yong | H01M 4/131 429/231.5 |
| 2014/0175337 A1* | 6/2014 | Chern | C07D 207/452 252/506 |

FOREIGN PATENT DOCUMENTS

| | | |
|---|---|---|
| CN | 1930706 A | 3/2007 |
| CN | 1972782 A | 5/2007 |

(Continued)

OTHER PUBLICATIONS

F. Yu et al., "Effects of initial composition and temperature on the kinetics of polymerizations of N,N'-bismaleimide-4,4'-diphenylmethane with barbituric acid," Journal of the Taiwan Institute of Chemical Engineers, v. 52, Jul. 2015, pp. 181-190.

(Continued)

*Primary Examiner* — Barbara L Gilliam
*Assistant Examiner* — Angela J Martin
(74) *Attorney, Agent, or Firm* — Mintz Levin Cohn Ferris Glovsky and Popeo, P.C.; Peter F. Corless; Joohee Lee

(57) ABSTRACT

An additive formulation for a lithium ion battery is provided, which includes an ionic conductor and a compound having a maleimide structure. An electrode slurry composition is also provided, which includes an active material, a conductive additive, an adhesive, and an additive formulation containing an ionic conductor and a compound having a maleimide structure modified by a compound having a barbituric acid structure.

16 Claims, 1 Drawing Sheet

(51) Int. Cl.
*H01M 10/05* (2010.01)
*H01M 4/13* (2010.01)
*H01M 4/62* (2006.01)
*C07D 207/452* (2006.01)
*H01M 4/525* (2010.01)
*H01M 10/0525* (2010.01)

(52) U.S. Cl.
CPC ......... *C07D 207/452* (2013.01); *H01M 4/525* (2013.01); *H01M 10/0525* (2013.01)

(56) References Cited

FOREIGN PATENT DOCUMENTS

| | | | | | |
|---|---|---|---|---|---|
| CN | 101212052 | A | 7/2008 | | |
| CN | 101841022 | A | 9/2010 | | |
| CN | 102569874 | A | 7/2012 | | |
| CN | 103094567 | A | 5/2013 | | |
| CN | 103880821 | A | 6/2014 | | |
| CN | 103880821 | A * | 6/2014 | ......... | C07D 207/452 |
| JP | 10-144302 | A2 | 5/1998 | | |
| JP | 10144302 | A2 | 5/1998 | | |
| JP | 11-135121 | | 5/1999 | | |
| JP | 2007-527603 | A | 9/2007 | | |
| JP | 2007527603 | A | 9/2007 | | |
| JP | 2010-157512 | A | 7/2010 | | |
| JP | 20100157512 | A | 7/2010 | | |
| JP | 2012-134149 | A | 7/2012 | | |
| JP | 2012134149 | A | 7/2012 | | |
| JP | 2014-026819 | * | 2/2014 | ........ | H01M 10/0525 |
| JP | 2014-026819 | A | 2/2014 | | |
| TW | I484685 | B | 5/2015 | | |

OTHER PUBLICATIONS

F. Yu et al., "Kinetics of polymerization of N,N'-bismaleimide-f,4'-diphenylmethane with barbituric acid," Journal of the Taiwan Institute of Chemical Engineers, v. 45, Mar. 2014, pp. 2820-2826.

F. Yu et al., "Effect of Solvent Proton Affinity on the Kinetics of Michael Adition Polymerization of N,N'-Bismaleimide-4,4'-Diphenylmethane with Barbituric Acid," Polymer Engineering and Science, v. 54, 2014, pp. 559-568.

Q. Pham et al., "Polymerization kinetics of reactive N,N'-bismaleimide-4,4'-diphenylmethane/barbituric acid based microgel particles," Thermochimica Acta, 2014, pp. 1-7.

M. Kotobuki et al., "Preparation of Li1-5Al0-5Ti1-5(PO4)3 solid electrolyte via coprecipitation using various PO4 sources," Materials Technology: Advanced Functional Materials, v. 29, Nov. 2014, pp. A93-A97.

J. Pan et al., "In-time Product of Green and Environmental Material Development of Nano STOBA Material for its Application," Journal of Taiwan Chemical Industry Association (TCIA), Issue 6, Jul. 2011, pp. 47-52.

Patil, V. et al., "Structural and Electrical Properties of NASICON Type Solid Electrolyte Nanoscaled Glass-Ceramic Powder by Mechanical Milling for Thin Film Batteries", Journal of Nanoscience and Nanotechnology, Vo. 13, 3665-3668 (2013).

Aono, H. et al., "Ionic Conductivity of the Lithium Titanium Phosphate (Lii+xMxTi2-x(PO4)3, M=Al, Sc, Y, and La) Systems", Journal of Electrochemical Society, vol. 136, No. 2, Feb. 1989.

* cited by examiner

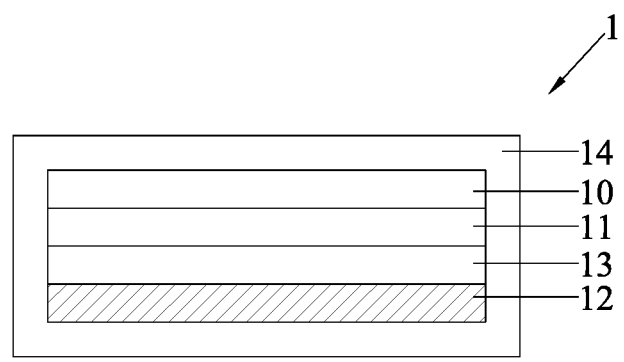

ADDITIVE FORMULATION AND COMPOSITION FOR LITHIUM ION BATTERY AND LITHIUM ION BATTERY COMPRISING THE SAME

CROSS-REFERENCE TO RELATED APPLICATION

The present disclosure is based on, and claims priority from Taiwan Application Number 104143336, filed Dec. 23, 2015, the disclosure of which is hereby incorporated by reference herein in its entirety.

TECHNICAL FIELD

The present disclosure relates to additive formulations, and more particularly, to an electrode paste composition and a lithium ion battery.

BACKGROUND

Lithium ion batteries or lithium polymer batteries have the same electrochemical principle as the general batteries, and each of the batteries consists essentially of an anode, a cathode, an insulating membrane and an electrolyte solution. Lithium ions move from the anode to the cathode during a charging process; and the lithium ions move from the cathode to the anode during a discharging process. Each of the anode and the cathode comprises a metal collecting board and a coating layer on the surface of the electrode, and both of the coating layers on the surfaces of the anode and the cathode contain electrode active materials, conductive powder and electrode adhesives.

Since the anode paste composition for preparing an anode surface coating layer contains metal oxide powder, such as, high density lithium cobalt oxide ($LiCoO_2$), for use as an anode active material with low density carbon powder and graphite, sedimentation can easily occur in the anode paste composition when the composition is mixed with and dispersed in polyvinylidene difluoride (PVDF) as an electrode adhesive and N-methylpyrrolidone (NMP) as a solvent. Therefore, maleimide modified with barbituric acid has been developed to increase its compatibility with the solvent in the electrode paste. However, a lithium battery prepared from the composition containing maleimide modified with barbituric acid also has limitations in resistance, causing unnecessary power consumption and reduction in capacitance during operation.

Accordingly, there is a need for a novel material for lithium ion batteries to meet the requirements of high capacitance, security high level of safety and a good cycle life.

SUMMARY

In accordance with one embodiment of the disclosure, an additive formulation is provided. The additive formulation for a lithium ion battery comprises an ionic conductor having the structure of Formula (I) and a compound having a maleimide structure modified by a compound having a barbituric acid structure:

$$Li_xM_yTi_z(PO_4)_3 \qquad \text{Formula (I)}$$

wherein M represents Al, Fe or Cr, and 0<x<2, 0<y≤1, and 0<z<3, and the weight ratio of the compound having the maleimide structure to the ionic conductor is from 1.0:0.5 to 1.0:5.0.

In accordance with one embodiment of the disclosure, an electrode paste composition is provided. The electrode paste composition comprises an active material, a conductive additive, an adhesive, and the aforementioned additive formulation.

In accordance with one embodiment of the disclosure, a lithium ion battery is provided. The lithium ion battery comprises an anode, the aforementioned electrode paste composition, a cathode and an electrolyte solution. The aforementioned electrode paste composition is disposed on the anode and the electrolyte solution is filled between the anode and the cathode.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein:

FIG. 1 is a sectional schematic view of a lithium ion battery illustrated in the Examples of the disclosure.

DETAILED DESCRIPTION

The implementation of the present disclosure will be illustrated by specific examples below, and a person skilled in the art can readily conceive the advantages and effects of the present disclosure based on content disclosed in the present specification.

In the present disclosure, an additive formulation for a lithium ion battery is provided. The additive formulation includes an ionic conductor combined with a compound having a maleimide structure modified by a compound having a barbituric acid structure. The ionic conductor includes a lithium ion, two kinds of metal ions, and phosphate. According to embodiments of the present disclosure, the additive formulation for a lithium ion battery can reduce the resistance of a battery.

In accordance with one embodiment of the disclosure, an additive formulation is provided. The additive formulation of the present disclosure includes an ionic conductor and a compound having a maleimide structure modified by a compound having a barbituric acid structure. The ionic conductor can be the structure of Formula (I):

$$Li_xM_yTi_z(PO_4)_3 \qquad \text{Formula (I)}$$

wherein M represents Al, Fe or Cr; and 0<x<2, 0<y≤1, and 0<z<3. The weight ratio of the compound having a maleimide structure to the ionic conductor is from 1.0:0.5 to 1.0:5.0.

In one embodiment, the ionic conductor is selected from $LiAlTi(PO_4)_3$, $LiFeTi(PO_4)_3$ and $LiCrTi(PO_4)_3$.

In one embodiment, the additive formulation for a lithium ion battery of the present disclosure, the compound having a maleimide structure is a polymaleimide compound having two or more maleimide structures. In another embodiment, the compound having a maleimide structure is a compound having a single maleimide structure.

In one embodiment, the compound having a maleimide structure is one modified with a compound having a barbituric acid structure and can be referred to as a modified maleimide, which is resulted from the reaction of the compound having a barbituric acid structure and a compound having a maleimide structure.

In order to obtain the modified maleimide, in one embodiment, the molar ratio of the compound having a maleimide structure to the compound having a barbituric acid structure is 25:1 to 1:1.

The compound having a barbituric acid structure of the present disclosure has the structure of Formula (II):

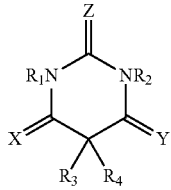
(II)

wherein X, Y and Z are all hydrogen atoms or at least one of X, Y and Z is replaced with a sulfur atom; and $R_1$, $R_2$, $R_3$ and $R_4$ are each independently selected from hydrogen and $C_1$-$C_5$ alkyl.

In one embodiment, X, Y and Z are all hydrogen atoms, both $R_3$ and $R_4$ are hydrogen, and $R_1$ and $R_2$ are each independently selected from hydrogen and $C_1$-$C_5$ alkyl, provided with that $R_1$ and $R_2$ are not hydrogen at the same time.

In another embodiment, at least one of X, Y and Z is replaced with a sulfur atom, and $R_1$, $R_2$, $R_3$ and $R_4$ are each independently selected from hydrogen and $C_1$-$C_5$ alkyl.

In addition, the compound having a maleimide structure or the compound having a maleimide structure for reacting with the compound having a barbituric acid structure is one having a polymaleimide structure and/or a single maleimide structure.

In one embodiment, the compound having a maleimide structure has the structure of Formula (III):

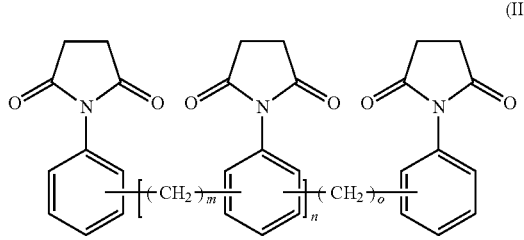
(III)

wherein m, n and o are each an integer of 0 or above, provided with that m, n and o are not 0 at the same time.

In another embodiment, m, n and o are each an integer more than 1.

In another embodiment, the compound having a maleimide structure has the structure of Formula (IV):

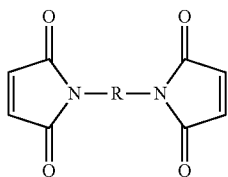
(IV)

wherein R is $C_1$-$C_{12}$ alkylene,

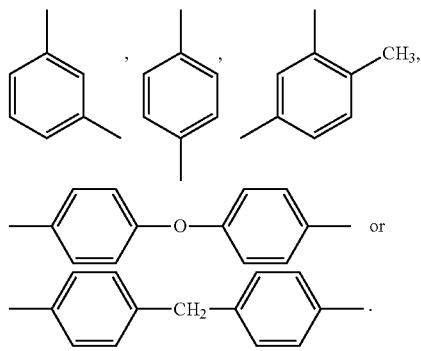

In one embodiment, the $C_1$-$C_{12}$ alkylene can be —$(CH_2)_2$—, —$(CH_2)_6$—, —$(CH_2)_8$—, —$(CH_2)_{12}$— or —$CH_2$—$C(CH_3)_2$—$CH_2$—$CH(CH_3)$—$(CH_2)_2$—.

In one embodiment, the compound having a maleimide structure is at least one selected from the group consisting of the following compounds having a single maleimide structure: phenylmaleimide, N-(p-methylphenyl)maleimide, N-(o-methylphenyl)maleimide, N-(m-methylphenyl)maleimide, N-cyclohexyl maleimide, maleimide, maleimidophenol, maleimidobenzocyclobutene, phosphorus-containing maleimide, phosphonate-containing maleimide, siloxane-containing maleimide, N-(4-tetrahydropyranyl-oxyphenyl) maleimide and 2,6-xylyl-maleimide.

For example, propylene carbonate (PC) or N-methylpyrrolidone (NMP) is used as the solvent in the modification of modified maleimide; wherein the weight ratio of the total weight of the compound having a barbituric acid structure and the compound having maleimide structure to the solvent is in a range of 3:97 to 40:60. The modification can be carried out at a temperature of 110 to 130° C. for 2 to 7 hours.

In one embodiment, the additive formulation for a lithium ion battery can be used in an anode formulation composite material, a cathode formulation composite material, an electrolyte formulation composite material or an insulating membrane coating formulation composite material of a lithium ion battery.

The electrode paste composition of the present disclosure comprises an active material, a conductive additive, an adhesive, and the aforementioned additive formulation containing an ionic conductor and a compound having a maleimide structure.

In the electrode paste composition of the present disclosure, the active material can be an anode active material, for example, but not limited to, Li—Ni—Co—Al (NCA), Li—Ni—Co—Mn (LNCM), lithium cobalt oxide ($LiCoO_2$), lithium manganese oxide ($LiMnO_2$), lithium nickel oxide ($LiNiO_2$), lithium iron phosphate($LiFePO_4$), and a mixture of two or more of the above.

The present disclosure can also use a cathode active material, including mesophase carbon microbeads (MCMB), natural graphite powder and a mixture thereof as an active material of the paste.

In the electrode paste composition of the present disclosure, the content of the active material is not particularly limited, as long as it is sufficient to provide capacitance required without affecting processing properties of an electrode film. In one embodiment, the active material can be 20 to 80 wt %. In one embodiment, the active material can be 40 to 70 wt %, based on the total weight of the electrode paste composition.

In the electrode paste composition of the present disclosure, the examples of the conductive additive include, but not limited to, at least one of granular graphite KS4 (4 μm), granular graphite KS6 (6 μm), vapor grown carbon fiber (VGCF), and small particle carbon black (SP). Generally, VGCF is used.

A functional group containing a double bond capable of reacting with maleimide can be imparted to the surface of the additive formulation by introducing the functional group into the conductive additive through a surface treatment. For example, an amino (—NH$_2$) functional group or a functional group containing an ethylenically double bond (—CH=CH$_2$) capable of reacting with a modified maleimide dispersant is imparted to the surface of the conductive additive by modifying the conductive additive with a silane coupling agent or an oleic acid coupling agent. In general, the conductive additive is 0.1 to 5 wt %, based on the total weight of the electrode paste composition.

In the electrode paste composition of the present disclosure, examples of the adhesive include, but not limited to, polyvinylidene difluoride (PVDF), acrylic resins and styrene-butadiene rubber (SBR), and at least one adhesive can be used. The adhesive can be mixed with the modified maleimide dispersant to form a uniform net structure, so as to improve the coating property of the paste. In one embodiment, the adhesive is 0.1 to 5 wt %, based on the total weight of the electrode paste composition. The electrode paste composition can further comprise other additives, such as a surfactant; and a reaction initiator, such as peroxide and 2,2'-azobisisobutyronitrile (AIBN).

According to above, the present disclosure provides a lithium ion battery. As shown in FIG. 1, a lithium ion battery 1 comprises: an anode 10; an electrode paste composition 11 formed on the anode 10; a cathode 12; and an electrolyte solution 13 filled between the anode 10 and the cathode 12. In addition, the lithium ion battery 1 can further comprise a package 14 for sealing the anode 10, the cathode 12 and the electrolyte solution 13, and the package 14 can be a resin or a composite of a resin and a metal.

In one embodiment, the active material in the electrode paste composition is a lithium cobalt oxide, the ionic conductor is LiAlTi(PO$_4$)$_3$, and the compound having a maleimide structure is one modified with a compound having a barbituric acid structure.

In the electrode paste composition of the present disclosure, the modified maleimide has a dendrimer-like hyper-branched structure which can form a stable complex with an active material such as metal oxide in the electrode paste composition to increase dispersibility and maintain stable viscosity in the long term, in the additive formulation containing an ionic conductor and a compound having a maleimide structure.

In the electrode paste composition of the present disclosure, by using an additive formulation containing an ionic conductor and a compound having a maleimide structure, the introduction of the ionic conductor provides a conductive channel and a driving force for a leaping pathway of lithium ions, such that the conduction of the lithium ions under the action of an electric field or a voltage is accelerated. Thus, for a lithium battery using the additive formulation (organic phase) containing barbituric acid-modified maleimide, the defects of increased resistance caused by the additive formation can be resolved to make the battery have the battery property of low resistance, such that unnecessary power consumption during operation can be avoided and the operating efficiency of the battery can be effectively increased, while maintaining high capacitance, a high level of safety and an excellent cycle life.

The following examples are used for illustration of the present disclosure, but the claims of the present disclosure are not limited thereto. The present disclosure can also be performed or applied by other different implementations, and various modifications and alterations can also be made to various details in the present specification based on different views and applications, without departing from the spirit of the present disclosure.

EXAMPLES

Synthetic Example 1. Preparation of polymaleimide

Bismaleimide and N-methylpyrrolidone (NMP) as solvents were mixed at a weight ratio of 3: 97, and then the mixture was reacted at 130° C. for about 24 hours. Thereafter, polymaleimide with N-methylpyrrolidone as the solvent was obtained and further used as a component of an additive formulation. The bismaleimide is the compound of Formula (V) below:

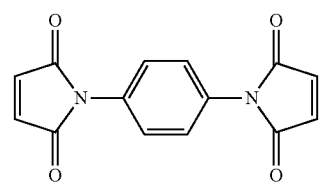

Formula (V)

Synthetic Example 2. Preparation of modified maleimide

Bismaleimide and barbituric acid (BTA) (molar ratio of 2:1) were added in N-methylpyrrolidone, wherein the weight ratio of (bismaleimide+barbituric acid) to N-methylpyrrolidone was 20: 80, and the mixture was reacted at 130° C. for about 3 hours. Thereafter, modified maleimide with N-methylpyrrolidone as the solvent was obtained further used as a component of an additive formulation. The bismaleimide is a compound of Formula (V) below:

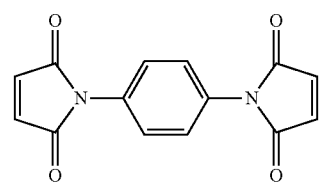

Formula (V)

Example 1. Preparation of an Additive Formulation Containing an Ionic Conductor and a Compound Having a Maleimide Structure for a Lithium Ion Battery First of all, 671.2 g of lithium cobalt oxide (LiCoO$_2$), 17.4 g of a conductive additive (Super P), 13.9 g of an adhesive (PVDF) and an additive formulation containing 7 g of the modified maleimide of Synthetic Example 2 and 14 g of an ionic conductor (LiAlTi(PO$_4$)$_3$ (synthesized and provided by the Laboratory of Professor Li Guanghua at Chemistry department, National Central University, Taiwan) (weight ratio of 1: 2) were mixed in a planetary mixer to obtain an anode paste for a standard lithium ion battery. Then, the anode paste was coated on the surface of an aluminum foil according to a preparation method for an anode plate of a standard lithium ion battery to obtain the anode plate.

In addition, a cathode paste and a cathode plate were prepared according to a preparation method for a cathode plate of a standard lithium ion battery, i.e., 930 g of mesocarbon microbeads (MCMB 2528), 20 g of conductive graphite (KS4), 60 g of polyvinylidene difluoride (PVDF), 45 g of oxalic acid and 750 g of N-methylpyrrolidone were mixed in a planetary mixer to obtain a cathode paste, and then the cathode paste was coated on a copper foil surface to obtain the cathode plate.

Thereafter, the anode plate and the cathode plate were assembled to obtain a standard battery core (Jelly Roll, 503759C) with a size of 5 mm (height)×37 mm (width)×59 mm (length), 4.2 g of a liquid standard electrolyte solution (PC/EC (ethylene carbonate)/DEC (diethyl carbonate)=2/3/5 (volume ratio), added with 1.1M $LiPF_6$ and 2.0 wt % vinylene carbonate (VC)) was filled thereto, and then it was packaged and aged to form the lithium ion battery of Example 1.

Comparative Example 1. Preparation of an Additive Formulation Containing a Compound Having a Maleimide Structure for a Lithium Ion Battery A lithium ion battery was prepared by the method of Example 1, except that the additive formulation containing modified maleimide and an ionic conductor of Synthetic Example 2 was replaced with the modified maleimide of Synthetic Example 2.

Comparative Example 2. Preparation of an Additive Formulation Containing a Compound Having a Maleimide Structure for a Lithium Ion Battery A lithium ion battery was prepared by the method of Example 1, except that the additive formulation containing modified maleimide and an ionic conductor of Synthetic Example 2 was replaced with the polymaleimide of Synthetic Example 1.

Test Example 1. Performance Test on Lithium Ion Batteries

Evaluation of the performance of the batteries was performed using stable current program at a charge-discharge rate of 1C. During the test, the first discharge capacity, the resistance, and the residual capacity (the discharge capacity after the last charging process) after 500 charge-discharge cycles (for each cycle, discharging over 1 hour and charging for 1 hour) at room temperature, and the residual capacity after 500 charge-discharge cycles at 55° C. for each of the batteries is recorded in Table 1.

TABLE 1

| | Performance of battery products | | | |
|---|---|---|---|---|
| | First discharge capacity (mAh) | Resistance (mΩ) | Residual capacity after 1 C/1 C 500 charge-discharge cycles (Room temperature) (%) | Residual capacity after 1 C/1 C 500 charge-discharge cycles (at 55° C.) (%) |
| Ex. 1 | 1349 | 30 | 92 | 86 |
| Comp. Ex. 1 | 1306 | 34 | 88 | 74 |
| Comp. Ex. 2 | 1345 | 30 | 83 | 68 |

It can be seen from the data in Table 1 that the lithium ion battery using modified maleimide of Comparative Example 1 still maintained higher residual capacity after multiple cycles, as compared to that of the lithium ion battery without using modified maleimide of Comparative Example 2. However, the use of modified maleimide as an additive formulation for a lithium ion battery in Comparative Example 1 also resulted in the defect of increased resistance. In the view of the lithium ion batteries using the additive formulation containing an ionic conductor and modified maleimide of Example 1, the induction of the ionic conductor provides a conductive channel and a driving force for a leaping pathway of lithium ions, such that the conduction of the lithium ions under the action of an electric field or a voltage is accelerated. Thus, the defect of increased resistance caused by additive formulations containing modified maleimide can be resolved to make batteries each having the battery property of low resistance.

Test Example 2. Discharge (C-Rate) Test on Lithium Ion Batteries

A standard current program was performed at room temperature, and the first discharge capacity at each of the charge-discharge rates of 0.2C, 1C, 2C, 3C, 5C and the residual capacity for each after the third discharge under different currents are recorded in Table 2.

TABLE 2

| | First discharge capacity (mAh) | 0.2 C | 1 C | 2 C | 3 C | 5 C |
|---|---|---|---|---|---|---|
| Ex. 1 | 1349 | 100% | 98% | 83% | 55% | 48% |
| Comp. Ex. 1 | 1306 | 100% | 95% | 80% | 50% | 36% |
| Comp. Ex. 2 | 1345 | 100% | 98% | 83% | 56% | 48% |

It can be seen from Table 2 that the application of the additive formulation containing an ionic conductor and modified maleimide to a lithium ion battery can improve electric capacity of the battery.

Test Example 3. Safety Test on Lithium Ion Batteries

A safety test was performed on lithium ion batteries by using a needle with a diameter of 2.5 mm at a puncturing rate of 1 mm/S, and the test results are recorded in Table 3.

TABLE 3

| | Explosion with sparks | Temperature of battery center during puncturing (° C.) |
|---|---|---|
| Ex. 1 | No | 133 |
| Comp. Ex. 1 | No | 142 |
| Comp. Ex. 2 | Yes | 695 |

It can be seen from the data in Table 3 that the lithium ion batteries using the additive formulations containing an ionic conductor and modified maleimide were safe.

In the electrode paste composition of the present disclosure, the use of the additive formulation containing an ionic conductor and a compound having a maleimide structure can substantially resolve the defect of increased resistance caused by the additive formulation containing barbituric acid-modified maleimide for a lithium ion battery. Therefore, a lithium ion battery with low resistance (which can avoid excessive power self-consumption and energy loss during operation), a high level of safety, high capacitance, and an excellent cycle life at room temperature or a high temperature can be prepared. The totally commercialized lithium batteries broadly used in the electric storage industry and electric vehicles can provide a safe and green energy source with high efficiency to solve the problems of increasingly exhausted petroleum resource and environmental pollution due to the global greenhouse effect.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An additive formulation for a lithium ion battery, comprising:
    an ionic conductor, which is at least one selected from the group consisting of $LiAlTi(PO_4)_3$, $LiFeTi(PO_4)_3$ and $LiCrTi(PO_4)_3$; and
    a compound having a maleimide structure modified by a compound having a barbituric acid structure, wherein a weight ratio of the compound having the maleimide structure to the ionic conductor is from 1.0: 0.5 to 1.0: 5.0.

2. The additive formulation of claim 1, wherein the compound having the maleimide structure is a polymaleimide compound having two or more maleimide structures.

3. The additive formulation of claim 1, wherein the compound having the barbituric acid structure has a structure of Formula (II):

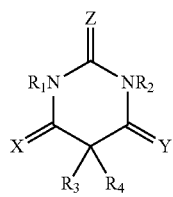

(II)

wherein all of X, Y and Z are oxygen atoms or at least one of X, Y and Z is replaced by a sulfur atom, and $R_1$, $R_2$, $R_3$ and $R_4$ are each independently selected from the group consisting of hydrogen and $C_1$-$C_5$ alkyl.

4. The additive formulation of claim 3, wherein all of X, Y and Z are oxygen atoms, $R_3$ and $R_4$ are both hydrogen, and $R_1$ and $R_2$ are each independently selected from the group consisting of hydrogen and $C_1$-$C_5$ alkyl, provided that $R_1$ and $R_2$ are not both hydrogen at the same time.

5. The additive formulation of claim 1, wherein the compound having the maleimide structure has a structure of Formula (III):

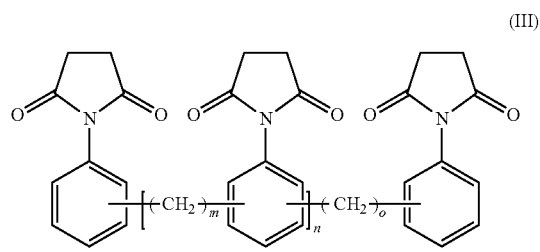

(III)

wherein m, n and o are each an integer of 0 or above, and m, n and o are not 0 at the same time.

6. The additive formulation of claim 1, wherein the compound having the maleimide structure has a structure of Formula (IV):

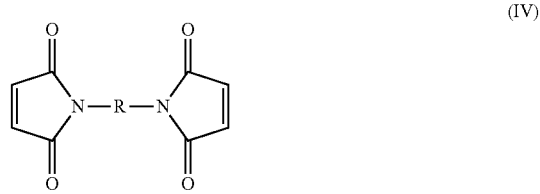

(IV)

wherein R is $C_1$-$C_{12}$ alkylene,

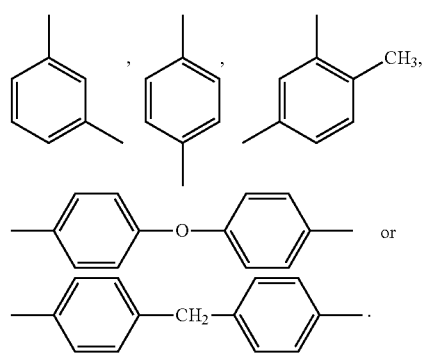

7. The additive formulation of claim 1, wherein the compound having the maleimide structure is at least one selected from the group consisting of the following compounds having a single maleimide structure: phenylmaleimide, N-(p-methylphenyl) maleimide, N-(o-methylphenyl) maleimide, N-(m-methylphenyl)maleimide, N-cyclohexyl maleimide, maleimide, maleimidophenol, maleimidobenzocyclobutene, phosphorus-containing maleimide, phosphonate-containing maleimide, siloxane-containing maleimide, N-(4-tetrahydropyranyl-oxyphenyl)maleimide and 2,6-xylyl-maleimide.

8. An electrode paste composition, comprising:
an active material;
a conductive additive;
an adhesive; and
the additive formulation of claim 1.

9. The electrode paste composition of claim 8, wherein the active material is an anode active material or a cathode active material.

10. The electrode paste composition of claim 8, wherein the active material is at least one selected from the group consisting of Li—Ni—Co—Al (NCA), Li—Ni—Co—Mn (LNCM), lithium cobalt oxide ($LiCoO_2$), lithium manganese oxide ($LiMnO_2$), lithium nickel oxide ($LiNiO_2$) and lithium iron phosphate ($LiFePO_4$).

11. The electrode paste composition of claim 8, wherein the active material is in an amount of from 20 to 80 wt %, based on a total weight of the electrode paste composition.

12. The electrode paste composition of claim 8, wherein the conductive material is in an amount of from 0.1 to 5 wt %, based on a total weight of the electrode paste composition.

13. The electrode paste composition of claim 8, wherein the adhesive is in an amount of from 0.1 to 15 wt %, based on a total weight of the electrode paste composition.

14. The electrode paste composition of claim 8, wherein the additive formulation is in an amount of from 1 to 10 wt%, based on a total weight of the electrode paste composition.

15. A lithium ion battery, comprising:

an anode;

the electrode paste composition of claim 9 formed on the anode;

a cathode; and an electrolyte solution filled between the anode and the cathode.

16. The lithium ion battery of claim 15, wherein the active material of the electrode paste composition is lithium cobalt oxide.

* * * * *